US010836705B1

(12) United States Patent
Coveney

(10) Patent No.: US 10,836,705 B1
(45) Date of Patent: Nov. 17, 2020

(54) PROCESS FOR THE PRODUCTION OF BRETYLIUM TOSYLATE

(71) Applicant: TopChem Pharmaceuticals Limited, Ballymote (IE)

(72) Inventor: Donal Coveney, Ballymote (IE)

(73) Assignee: TOPCHEM PHARMACEUTICALS LIMITED, Ballymote (IE)

( * ) Notice: Subject to any disclaimer, the term of this patent is extended or adjusted under 35 U.S.C. 154(b) by 0 days.

(21) Appl. No.: 16/540,595

(22) Filed: Aug. 14, 2019

(51) Int. Cl.

| | |
|---|---|
| ***C07C 209/84*** | (2006.01) |
| ***C07C 211/63*** | (2006.01) |
| ***C07C 209/22*** | (2006.01) |
| ***C07C 209/04*** | (2006.01) |
| ***C07C 209/08*** | (2006.01) |
| ***C07C 211/29*** | (2006.01) |

(52) U.S. Cl.
CPC .......... *C07C 209/84* (2013.01); *C07C 209/04* (2013.01); *C07C 209/08* (2013.01); *C07C 209/22* (2013.01); *C07C 211/63* (2013.01); *C07C 211/29* (2013.01)

(58) Field of Classification Search
None
See application file for complete search history.

(56) References Cited

U.S. PATENT DOCUMENTS 3,038,004 A 6/1962 Copp et al.

OTHER PUBLICATIONS

Acetone, downloaded from: https://pubchem.ncbi.nlm.nih.gov/compound/Acetone#section=Boiling-Point&fullscreen=true, on Mar. 24, 2020 (Year: 2020).*
Simon ("6. Synthesis of o-bromobenzyldimethylethylammonium salts with sympatholytic and hypotensive action" Meditsinskaya Promyshlennost SSSR, vol. 15, No. 7, p. 10-14, 1961) (Year: 1961).*
English language translation of Simon ("6. Synthesis of o-bromobenzyldimethylethylammonium salts with sympatholytic and hypotensive action" Meditsinskaya Promyshlennost SSSR, vol. 15, No. 7, p. 10-14, 1961) (Year: 1961).*
Sindelar ("Potential antidepressants. Synthesis of 6,11-dihydrodibenzo[b,e]thiepin-11-yl 4-(dimethylamino-methyl)phenyl ketone and of some related compounds" Journal of Heterocyclic Chemistry, vol. 26, issue 5, 1989, p. 1325-1330) (Year: 1989).*

* cited by examiner

*Primary Examiner* — Amy C Bonaparte
(74) *Attorney, Agent, or Firm* — Hoffman Warnick LLC

(57) ABSTRACT

A method of producing pharmaceutical grade bretylium tosylate comprising low amounts of mutagenic impurities. The method comprises forming bretylium tosylate having a purity of less than 99.5% and purifying the bretylium tosylate by: i) forming a slurry of the bretylium tosylate with a mixture of acetone and ethyl acetate; ii) filtering the slurry to obtain purified bretylium tosylate. The bretylium tosylate so produced has a purity of at least 99.5%, and suitably comprises less than 0.5 ppm of the potentially mutagenic impurity ethyl p-toluenesulfonate. The bretylium tosylate so produced also suitably comprises less than 0.5 ppm of the potentially mutagenic impurity 2-bromobenzylbromide.

10 Claims, No Drawings

PROCESS FOR THE PRODUCTION OF BRETYLIUM TOSYLATE

FIELD

The present invention relates to a method of producing high purity bretylium tosylate and to high purity bretylium tosylate produced by said method. In particular the present invention relates to a method of producing bretylium tosylate with reduced amounts of mutagenic impurities such as ethyl p-toluenesulfonate and 2-bromobenzylbromide.

BACKGROUND

Bretylium tosylate is an approved antiarrhythmic pharmaceutical agent (see FDA Approved Drug Products, 39th Edition (2019)) and is indicated for the prophylaxis and therapy of ventricular fibrillation; and for the treatment of life-threatening ventricular arrhythmia that has failed to respond to other first-line antiarrhythmic agents.

Bretylium tosylate may be prepared in a two-step synthesis described in U.S. Pat. No. 3,038,004 involving reaction of 2-bromobenzyl bromide with dimethylamine to produce the intermediate (2-bromobenzyl)-dimethylamine. Further treatment with ethyl p-toluene sulfonate generates the crystalline bretylium tosylate.

The presence of mutagenic impurities in pharmaceutical drug substances and drug preparations is of major concern and is now strictly controlled (see ICH Harmonised Guideline M7 (R1), Mar. 31, 2017, “Assessment and control of DNA reactive (mutagenic) impurities in pharmaceuticals to limit potential carcinogenic risk”). The key raw materials in the bretylium tosylate synthesis, namely ethyl p-toluenesulfonate and 2-bromobenzyl bromide, are both strong alkylating agents and are considered mutagenic.

The known processes discussed above produce bretylium tosylate with elevated levels of the two mutagenic impurities: ethyl p-toluenesulfonate and 2-bromobenzyl bromide. Following the European recall of Nelfinavir Mesylate in 2007 due to the presence of the genotoxic impurity ethyl mesylate, the presence of such impurities in active pharmaceutical ingredients has come under sharp focus. The European Medicines Agency introduced strict guidelines in 2007 to restrict and control such impurities in active pharmaceutical ingredients. The US Food & Drug Administration then introduced similar guidelines in 2008. The internationally recognised standards for such potentially genotoxic impurities is now well established. The ICH guideline limit for the daily intake of a suspected genotoxic impurity is set at 1.5 μg.

Ethyl p-toluenesulfonate is a strong alkylating agent and is therefore an alert for genotoxicity. As ethyl p-toluenesulfonate is a key starting material used in the final synthetic step in the process for manufacturing bretylium tosylate, this is a likely impurity in the bretylium tosylate drug substance.

The maximum daily dose of bretylium tosylate is calculated at 2,800 mg, based on the dosage of 10 mg/kg for every 6 hours for an average 70 kg adult. By applying the ICH daily limit of 1.5 μg, a limit of 0.00005% (0.5 ppm) for ethyl p-toluenesulfonate is therefore calculated in the bretylium tosylate drug substance.

2-Bromobenzylbromide is also a strong alkylating agent and a potential genotoxic impurity. This substance is a key starting material in the first step of bretylium tosylate synthesis and is therefore a potential impurity in the bretylium tosylate drug substance. A limit of 0.00005% (0.5 ppm) for 2-bromobenzylbromide is similarly calculated for the bretylium tosylate drug substance based on the ICH guideline of no more than 1.5 μg per day.

A simple economic method for the production of Bretylium Tosylate meeting current strict requirements for genotoxic impurities is therefore highly desirable.

SUMMARY OF THE INVENTION

U.S. Pat. No. 3,038,004 (1962) teaches a method for the synthesis of bretylium tosylate whereby 2-bromobenzyl bromide is reacted with dimethylamine in a methanol solution. Fractional distillation of the crude reaction mixture yields (2-bromobenzyl)-dimethylamine which is then heated with ethyl p-toluenesulfonate to form bretylium tosylate which is isolated in purified from by crystallisation.

The boiling point of 2-bromobenzyl bromide at 129° C. at 19 mm/Hg is quite close to that of the intermediate (2-bromobenzyl)-dimethylamine at 108-112° C. at 20 mm. Therefore it has not proved to be possible to remove sufficient quantities of 2-bromobenzyl bromide impurities from (2-bromobenzyl)-dimethylamine using distillation. The present inventor has established that this process does not produce bretylium tosylate that will meet the current regulatory requirement for less than 0.5 ppm of both ethyl p-toluenesulfonate or 2-bromobenzyl bromide.

It is one aim of the present invention, amongst others, to provide a method of producing high purity bretylium tosylate that addresses at least one disadvantage of the prior art, whether identified here or elsewhere, or to provide an alternative to existing methods.

For instance it may be an aim of the present invention to provide a method of producing high purity bretylium tosylate which provides pharmaceutical grade bretylium tosylate with exceptionally low levels of mutagenic impurities ethyl p-toluenesulfonate and 2-bromobenzylbromide.

According to aspects of the present invention, there is provided a method and product as set forth in the appended claims. Other features of the invention will be apparent from the dependent claims, and the description which follows.

According to a first aspect of the present invention, there is provided a method of producing bretylium tosylate having a purity of at least 99.5%, the method comprising:

a) providing bretylium tosylate having a purity of less than 99.5%;

b) purifying the bretylium tosylate by:

i) forming a slurry of the bretylium tosylate with a mixture of acetone and ethyl acetate; and ii) filtering the slurry to obtain purified bretylium tosylate.

Suitably the steps of the method are carried out in the order step a) followed by step b).

After intensive investigations to solve the problem discussed above, the inventors have found that the method of this first aspect can provide pharmaceutical grade bretylium tosylate with non-detectable levels of the mutagenic impurity ethyl p-toluenesulfonate. This provides the bretylium tosylate active pharmaceutical ingredient (API) with an improved safety profile for which meets the regulatory criteria for use in humans.

The inventors found that acetone is an excellent solvent to dissolve and crystallise bretylium tosylate but the recovery yield is low. Ethyl acetate was found to act as an anti-solvent and can be used to improve the recovered yield. This provides a product containing between 100 and 200 ppm of residual ethyl p-toluenesulfonate. Alternative solvents to ethyl acetate are diethyl ether, methyl tert-butyl ether or toluene.

Performing two further recrystallizations from acetone-ethyl acetate may bring the residual ethyl p-toluene sulfonate levels down to below the desired 0.5 ppm. However, this provides an uneconomical process due to the unfavourable throughput, cost and overall yield of the method. By forming a slurry of the bretylium tosylate with a mixture of acetone and ethyl acetate and filtering the slurry in steps i) and ii) of the method of this first aspect, the ethyl p-toluenesulfonate can be rapidly removed in a more economical way to provide high purity bretylium tosylate comprising exceptionally low amounts of mutagenic ethyl p-toluenesulfonate.

If ethyl acetate alone or other solvents are used, the slurrying process is much less efficient. If acetone alone is used, the yield losses of bretylium tosylate are unacceptably high.

Suitably the mixture of acetone and ethyl acetate comprises a ratio of acetone to ethyl acetate of from 1:1 to 1:5, suitably a ratio of from 1:2 to 1:4. Suitably the mixture of acetone and ethyl acetate comprises a ratio of acetone to ethyl acetate of approximately 1:3, suitably of 1:3.

Suitably step i) involves stirring the slurry for at least 20 minutes, suitably for at least 30 minutes. Suitably step i) involves stirring the slurry for from 30 to 60 minutes.

In some embodiments steps i) and ii) are repeated at least once.

The residual ethyl p-toluenesulfonate levels in the bretylium tosylate are determined by HPLC. The 0.00005% (0.5 ppm) test limit is achievable with a limit of detection of 0.02 ppm and a limit of quantitation of 0.07 ppm.

In the method of this first aspect, step ii) is suitably followed by a step iii) of recrystallizing the purified bretylium tosylate, suitably from a mixture of acetone and ethyl acetate. This further recrystallization from acetone-ethyl acetate provides a further removal of the ethyl p-toluenesulfonate to non-detectable levels.

The purified bretylium tosylate produced by this method suitably comprises less than 0.5 ppm of ethyl p-toluenesulfonate. Suitably the purified bretylium tosylate comprises less than 0.2 ppm of ethyl p-toluenesulfonate, suitably less than 0.1 ppm, suitably less than 0.05 ppm.

The method of this first aspect provides bretylium tosylate having a purity of at least 99.5%, suitably a purity of at least 99.9%.

Step a) of providing the bretylium tosylate having a purity of less than 99.5% suitably comprises steps:

a1) reacting 2-bromo-benzylbromide with dimethylamine in an organic solvent to form a crude reaction product solution of (2-bromobenzyl)-dimethylamine;

a2) treating the crude reaction product solution of (2-bromobenzyl)-dimethylamine with acid to convert the (2-bromobenzyl)-dimethylamine to an acid salt and separating the crude reaction product solution between an organic phase and an aqueous phase;

a3) removing the organic phase from the aqueous phase;

a4) treating the aqueous phase with base to convert the (2-bromobenzyl)-dimethylamine salt to a neutral (2-bromobenzyl)-dimethylamine; and a5) separating the neutral (2-bromobenzyl)-dimethylamine from the aqueous phase to provide purified (2-bromobenzyl)-dimethylamine.

Suitably the steps are carried out in the order step a1) followed by step a2) followed by step a3), followed by step a4), followed by step a5).

Suitably step a1) involves adding a solution of 2-bromobenzylbromide to a solution of dimethylamine. Suitably the solution of dimethylamine is an aqueous solution. The solution of dimethylamine is preferably a commercially available 40% aqueous solution, but other concentrations can be used successfully.

Step a1) suitably involves dissolving 2-bromobenzyl bromide in a suitable organic solvent and adding this solution to an aqueous solution of dimethylamine. The organic solvent is preferably methyl tert-butyl ether but any ether, hydrocarbon, ketone or chlorinated hydrocarbon solvent which is not miscible with water and is stable to strong bases and strong acids may be used. Such solvents include but are not restricted to diethyl ether, methyl cyclopentyl ether, 2-methyl-THF, toluene, dichloromethane, chloroform, 1,2-dichloroethane and methyl isobutyl ketone.

An excess of dimethylamine is used to obtain high conversion to the desired intermediate (2-bromobenzyl)-dimethylamine. Two to six mole equivalents of dimethylamine can be used, but 2.5-2.7 equivalents are preferred.

This two phase reaction suitably proceeds at room temperature and is 98% complete within a few hours. It is not possible to completely convert all of the 2-bromobenzyl bromide even with a large excess of dimethylamine, leading to concerns on residual 2-bromobenzylbromide in the final product, as discussed above.

Step a2) involves treating the crude reaction product solution of (2-bromobenzyl)-dimethylamine with acid. This suitably involves lowering the pH of the crude reaction product solution to less than 5, suitably to 4 or lower. This acidification of the reaction mixture with a suitable acid converts the product (2-bromobenzyl)-dimethylamine to a water soluble acid salt. The residual 2-bromobenzyl bromide remains in the organic layer. A suitable acid is concentrated hydrochloric acid but other acids such as sulfuric, phosphoric, citric or methane sulfonic acid may be used.

Step a3) of removing the organic phase from the aqueous phase suitably involves extracting the aqueous phase with further portions of organic solvent, for example methyl tert-butyl ether, to ensure traces of 2-bromobenzyl bromide or other neutral organic impurities are efficiently removed from the aqueous phase.

Step a4) of treating the aqueous phase with base suitably increases the pH of the aqueous phase to above 8. This neutralises the acidic aqueous phase. A suitable base is sodium hydroxide. The base is preferably sodium hydroxide but other bases such as potassium hydroxide, sodium carbonate or ammonium hydroxide solution may be used.

Neutralising the aqueous phase liberates the (2-bromobenzyl)-dimethylamine which separates as an oil. This oil may then be separated and the aqueous phase in step a5). The aqueous phase may then be extracted with further portions of organic solvent, for example with methyl tert-butyl ether, to remove any product remaining in the aqueous phase. The organic washings may then be combined with the oil separated from the aqueous phase to provide an organic solution of (2-bromobenzyl)-dimethylamine.

The organic solvent for the extraction is preferably methyl tert-butyl ether but any ether, hydrocarbon, ketone or chlorinated hydrocarbon solvent which is not miscible with water and is stable to strong bases and strong acids may be used. Such solvents include but are not restricted to diethyl ether, methyl cyclopentyl ether, 2-methyl-THF, toluene, dichloromethane, chloroform, 1,2-dichloroethane and methyl isobutyl ketone.

The organic solution of (2-bromobenzyl)-dimethylamine may then be washed with water and the solvent removed by distillation to provide the (2-bromobenzyl)-dimethylamine in high yield. Remarkably the purity of this (2-bromobenzyl)-dimethylamine is 99.5% or higher, by HPLC analysis.

A GC method was developed to detect trace levels of 2-bromobenzylbromide in the (2-bromobenzyl)-dimethylamine product. A limit of detection of 0.050 ppm and a limit of quantitation of 0.135 ppm was established. Using this analytical method, no residual 2-bromobenzyl bromide can be detected in the intermediate (2-bromobenzyl)-dimethylamine manufactured by the method of this first aspect.

Suitably the (2-bromobenzyl)-dimethylamine produced by steps a1) to a5) has a purity of at least 99.0%, suitably at least 99.5%, suitably by HPLC analysis.

Suitably, as a result of steps a1) to a5), the bretylium tosylate produced by the method of this first aspect comprises less than 0.5 ppm 2-bromobenzylbromide. Suitably the bretylium tosylate is substantially free of 2-bromobenzylbromide. Suitably 2-bromobenzylbromide is not detectable in the purified bretylium tosylate, suitably using the analytical techniques described herein.

Suitably step a5) is followed by a step a6) of reacting the purified (2-bromobenzyl)-dimethylamine with ethyl p-toluenesulfonate to form the bretylium tosylate.

Suitably no further purification step is carried out between step a5) and step a6). Therefore step a6) is suitably carried out on the product of the aqueous/organic separation process of steps a2) to a5).

In step a6), (2-bromobenzyl)-dimethylamine may be reacted with ethyl p-toluenesulfonate by heating without a solvent or in a suitable solvent such as acetone. A slight excess of ethyl p-toluenesulfonate may be used to ensure high levels of conversion of (2-bromobenzyl)-dimethylamine to bretylium tosylate. Ethyl acetate is added to the solution and on cooling, bretylium tosylate is isolated as a crystalline solid.

After step a6), step b) of purifying the bretylium tosylate by i) forming a slurry of the bretylium tosylate with a mixture of acetone and ethyl acetate; and ii) filtering the slurry to obtain purified bretylium tosylate, is carried out to obtain purified bretylium tosylate having a purity of at least 99.5% and suitably comprising less than 0.05 ppm of each of 2-bromobenzyl bromide and ethyl p-toluenesulfonate.

The overall yields are high and the process offers an economical method for the industrial manufacture of bretylium tosylate with exceptionally low levels of residual ethyl p-toluenesulfonate and 2-bromobenzyl bromide. Suitably the method of this first aspect provides a robust process to produce pharmaceutical grade bretylium tosylate with non-detectable levels of the mutagenic impurities: 2-bromobenzyl bromide and ethyl p-toluenesulfonate.

According to a second aspect of the present invention, there is provided a method of producing bretylium tosylate comprising less than 0.5 ppm 2-bromobenzylbromide, the method comprising:

a1) reacting 2-bromo-benzylbromide with dimethylamine in an organic solvent to form a crude reaction product solution of (2-bromobenzyl)-dimethylamine;

a2) treating the crude reaction product solution of (2-bromobenzyl)-dimethylamine with acid to convert the (2-bromobenzyl)-dimethylamine to an acid salt and separating the crude reaction product solution between an organic phase and an aqueous phase;

a3) removing the organic phase from the aqueous phase;

a4) treating the aqueous phase with base to convert the (2-bromobenzyl)-dimethylamine salt to a neutral (2-bromobenzyl)-dimethylamine;

a5) separating the neutral (2-bromobenzyl)-dimethylamine from the aqueous phase to provide purified (2-bromobenzyl)-dimethylamine; and a6) forming the bretylium tosylate comprising less than 0.5 ppm 2-bromobenzylbromide from the purified (2-bromobenzyl)-dimethylamine.

The method of this second aspect, and in particular the steps a1) to a6), may have any of the suitable features or advantages described in relation to the first aspect.

Suitably the steps of the method are carried out in the order step a1) followed by step a2), followed by step a3), followed by step a4), followed by step a5), followed by step a6).

Suitably the (2-bromobenzyl)-dimethylamine produced by steps a1) to a5) has a purity of at least 99.0%, suitably at least 99.5%, suitably by HPLC analysis.

Suitably step a6) involves reacting the purified (2-bromobenzyl)-dimethylamine with ethyl p-toluenesulfonate to form the bretylium tosylate.

According to a third aspect of the present invention, there is provided bretylium tosylate formed by a method of the first aspect, the bretylium tosylate having a purity of at least 99.5% and comprising less than 0.5 ppm of ethyl p-toluenesulfonate.

Suitably the bretylium tosylate is substantially free of ethyl p-toluenesulfonate.

Suitably the bretylium tosylate comprises less than 0.5 ppm 2-bromobenzylbromide. Suitably the bretylium tosylate is substantially free of 2-bromobenzylbromide.

According to a fourth aspect of the present invention, there is provided bretylium tosylate formed by a method of the second aspect, the bretylium tosylate having a purity of at least 99.5% and comprising less than 0.5 ppm 2-bromobenzylbromide.

Suitably the bretylium tosylate is substantially free of 2-bromobenzylbromide.

Suitably the bretylium tosylate comprises less than 0.5 ppm of ethyl p-toluenesulfonate. Suitably the bretylium tosylate is substantially free of ethyl p-toluenesulfonate.

According to a fifth aspect of the present invention, there is provided bretylium tosylate formed by a method of the first or second aspect, the bretylium tosylate having a purity of at least 99.5% and comprising less than 0.5 ppm 2-bromobenzylbromide and less than 0.5 ppm ethyl p-toluenesulfonate.

According to a sixth aspect of the present invention, there is provided a method of producing bretylium tosylate having a purity of at least 99.5% and comprising less than 0.5 ppm 2-bromobenzylbromide and less than 0.5 ppm ethyl p-toluenesulfonate, the method comprising:

a) forming bretylium tosylate by:

- a1) reacting 2-bromo-benzylbromide with dimethylamine in an organic solvent to form a crude reaction product solution of (2-bromobenzyl)-dimethylamine;
- a2) treating the crude reaction product solution of (2-bromobenzyl)-dimethylamine with acid to convert the (2-bromobenzyl)-dimethylamine to an acid salt and separating the crude reaction product solution between an organic phase and an aqueous phase;
- a3) removing the organic phase from the aqueous phase;
- a4) treating the aqueous phase with base to convert the acid salt of (2-bromobenzyl)-dimethylamine to a neutral (2-bromobenzyl)-dimethylamine;
- a5) separating the neutral (2-bromobenzyl)-dimethylamine from the aqueous phase to provide purified (2-bromobenzyl)-dimethylamine; and
- a6) reacting the purified (2-bromobenzyl)-dimethylamine with ethyl p-toluenesulfonate to form the bretylium tosylate;

b) purifying the bretylium tosylate by:

i) forming a slurry of the bretylium tosylate with a mixture of acetone and ethyl acetate; and ii) filtering the slurry to obtain purified bretylium tosylate.

The method of this sixth aspect may have any of the suitable features or advantages described in relation to the first and second aspects.

EXAMPLES

Synthetic scheme of bretylium tosylate

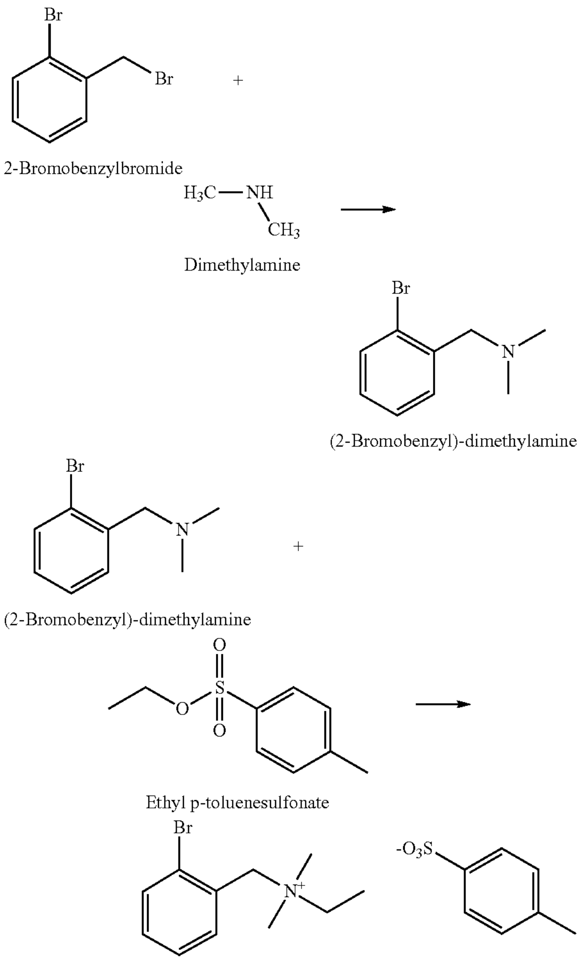

2-Bromobenzylbromide

Dimethylamine (2-Bromobenzyl)-dimethylamine (2-Bromobenzyl)-dimethylamine

Ethyl p-toluenesulfonate

Bretylium tosylate

Comparative Example 1: Standard Synthesis of (2-Bromobenzyl)-dimethylamine

A solution of 2-bromo-benzylbromide (1.0 kg) in methyl tert-butyl ether (2 litres) is slowly added to a 40% aqueous solution of dimethylamine (1.2 kg). A controlled addition rate is used to maintain the reaction temperature below 40° C. The two-phase reaction is stirred vigorously until substantially complete.

The layers are separated and the aqueous phase is washed with methyl tert-butyl ether. The combined methyl tert-butyl ether layers are then washed with water. The solvent is then removed under reduced pressure to yield (2-bromobenzyl)-dimethylamine as a clear mobile liquid (0.8 kg). Distillation under vacuum yields a clear oil (0.6 kg) with high levels of residual 2-bromobenzyl bromide.

Comparative Example 2: Standard Synthesis of Bretylium Tosylate (2-Bromobenzyl)-dimethylamine (0.6 kg) and ethyl p-toluenesulfonate (0.587 kg) are dissolved in acetone (1.2 litres) and then heated and stirred at reflux for 12 hours. Ethyl acetate (0.6 litres) is then added and the solution cooled to ambient to crystallise the product, Bretylium Tosylate.

The crude solid product is filtered and washed with ethyl acetate. The filtered solid is then dried under vacuum at 60° C. to yield Bretylium Tosylate (0.48 kilos) containing high levels of residual ethyl p-toluene sulfonate.

Example 3: Synthesis of (2-Bromobenzyl)-Dimethylamine with Low Levels of Residual Mutagenic Impurities A solution of 2-bromo-benzylbromide (3.0 kg) in methyl tert-butyl ether (6 litres) is slowly added to a 40% aqueous solution of dimethylamine (3.7 kg). A controlled addition rate is used to maintain the reaction temperature below 40° C. The two-phase reaction is stirred vigorously until substantially complete. The reaction is quenched by the careful addition of 37% aqueous hydrochloric acid until a pH of 1-3 is achieved. A controlled addition rate is used to maintain the reaction temperature below 40° C.

The layers are separated and the aqueous phase is washed with methyl tert-butyl ether. The methyl tert-butyl ether washes are discarded.

The aqueous phase is basified (to pH 9-13) with 20% aqueous sodium hydroxide. An oily layer forms and is separated. The aqueous phase is then extracted with methyl tert-butyl ether. The methyl tert-butyl ether extract is added to the first oily layer. The resulting solution is then washed with water. The solvent is then removed under reduced pressure to yield (2-bromobenzyl)-dimethylamine as a clear mobile liquid (2.4 kg) with no detectable levels of residual 2-bromobenzyl bromide.

Example 4: Synthesis of Bretylium Tosylate with Low Levels of Residual Mutagenic Impurities (2-Bromobenzyl)-dimethylamine (2.4 kg) and ethyl p-toluenesulfonate (2.35 kg) are mixed and then heated and stirred at 60° C. for 3 hours. The thick reaction mass is dissolved in acetone (10 litres). Ethyl acetate (5 litres) is then added and the solution cooled to ambient to crystallise the product, Bretylium Tosylate.

The crude solid product is filtered and the solid is suspended in a 1:3 acetone-ethyl acetate mixture (7 litres). The mixture is gently slurried for 30-60 minutes and the solid is filtered. This slurrying process is then repeated a further two times.

The final slurry is filtered and is washed with ethyl acetate. The filtered solid is then dried under vacuum at 60° C. to yield Bretylium Tosylate (4.3 kilos).

The Bretylium Tosylate is then recrystallised from acetone (9 litres) by heating to 50° C. until dissolution is complete. The solution is then transferred via a 1.0 μm in-line filter to a crystallisation vessel and ethyl acetate (4.5 litres) is added. The system is allowed to cool until crystallisation is complete.

The solid is filtered and the filtered solid is washed with ethyl acetate. The solid is then dried under vacuum at 50° C.-60° C. to yield purified Bretylium Tosylate (4.0 kilos) with no detectable levels of ethyl p-toluenesulfonate or 2-bromobenzyl bromide.

TABLE 1 purity data on three batches of Bretylium Tosylate
Table 1 below shows the purity of three different batches of Bretylium Tosylate produced according to the procedures of Examples 3 and 4. Each batch had a purity of at least 99.9% and the potentially mutagenic impurities 2-bromobenzylbromide and ethyl p-toluenesulfonate were not detectable in any of the batches.

| Impurity | Limit | T170313 | T180204 | T180301 |
|---|---|---|---|---|
| Ethyl p-toluenesulfonate[1] | 0.5 ppm | ND | ND | ND |
| (2-Bromobenzyl)-dimethylamine[1] | 1% | ND | ND | ND |
| Benzenesulfonic acid[1] | 0.10% | ND | 0.01% | ND |
| Individual unknown impurity[1] | ≤0.05% | Complies | Complies | Complies |
| Total impurities[1] | 2% | 0% | 0.01% | 0% |
| 2-Bromobenzyl-bromide[2] | 0.5 ppm | ND | ND | ND |
| Acetone[3] | 1000 ppm | 73 ppm | <24 ppm | 43 ppm |
| Ethyl acetate[3] | 5000 ppm | 110 ppm | 39 ppm | 77 ppm |
| Methyl tert-butyl ether[3] | 5000 ppm | <1 ppm | <2 ppm | 2 ppm |
| Residue on Ignition | 0.1% | 0% | 0% | 0% |
| Assay[1] | 98.0-101.0% | 100.0% | 99.8% | 100.3% |

[1]By HPLC.
[2]By GC.
[3]By GC headspace analysis

Analytical Method for the detection of Ethyl p-toluenesulfonate

HPLC Conditions:

Column: Zorbax SB phenyl, 5 μm, 4.6 mm×250 mm column or equivalent

Detector Wavelength: 265 nm

Flow Rate: 1.8 ml/min—Note: Start flow rate at 0.9 ml/min and gradually work up to 1.8 ml/min over a 40-50 min period.

Injection Volume: 200 μL

Run Time: 20 min.

Mobile Phase: Prepare a mixture of 0.01M Sodium 1-Octanesulfonate solution, Acetonitrile, glacial acetic acid and Triethylamine. (65:35:2:0.5).

Diluent Preparation: Prepare a mixture of 0.01M Sodium 1-Octanesulfonate solution, Acetonitrile, glacial acetic acid and Triethylamine (81:19:2:0.5)

Stock Standard Preparation: Dissolve 40 mg of accurately weighed ethyl p-toluenesulfonate standard to a 200 ml volumetric flask, dilute to volume with diluent and mix.

Working Standard Preparation: Take 2.5 ml of stock standard preparation and dilute to 200 ml with diluent. A further dilution of 1 ml of solution in 10 ml is carried out and made up to the mark with diluent (Concentration 0.00025 mg/ml)

Sample Preparation Transfer about 2.5 g of Bretylium Tosylate, accurately weighed, to a 5 ml volumetric flask, dissolve in and dilute to volume with diluent and mix.

The retention time of ethyl p-toluenesulfonate is about 10 minutes and the calculated limit of detection is 0.0000024% (0.024 ppm).

The area count for ethyl p-toluenesulfonate peak in the sample must not exceed the area count for that of the Working Standard solution.

Analytical Method for the detection of 2-bromobenzyl bromide

GC Conditions:

Column Phenomenex ZB-5 ms 30 m×0.32 mm×1 μm or equivalent

Injector Temperature: 280° C.

Detector Temperature: Flame Ionisation Detection at 280° C.

Column Temperature: 45° C. hold for 2 min. Ramp to 280° C. at 15° C. per/minute and hold for 10 minutes.

Column Flow 1.0 ml/min

Injection Volume 8.0 μL (split 1:10)

2-bromobenzyl bromide Stock Standard Solution (0.25 mg/ml): Accurately weigh 25 mg of 2-bromobenzyl bromide Reference standard in to a 100 ml volumetric flask and dilute to volume with Hexane.

2-bromobenzyl bromide Identification Standard Solution (0.0025 mg/ml): Further dilute 1 ml of 2-bromobenzyl bromide stock standard solution to 100 mls with hexane.

2-bromobenzyl bromide Working Standard solution (0.00025 mg/ml): Further dilute 1 ml of 2-bromobenzyl bromide identification standard solution to 10 mls with hexane. This working standard is the equivalent to the 0.00005% 2-bromobenzyl bromide specification.

Bretylium Tosylate Test Solution: Accurately weigh out 5.0 g of Bretylium Tosylate test material. Dissolve in 10 ml of purified water. Pipette 10 mls of hexane into this solution and shake vigorously. Allow the layers to separate and remove the top organic layer. Dry the organic layer with approximately 50-100 mgs of magnesium sulphate. Filter the resulting solution into a HPLC vial and analyse.

(2-Bromobenzyl)-dimethylamine Test Solution: Accurately weigh 5.0 g of (2-bromobenzyl)-dimethylamine. Add 10 ml of purified water and add concentrated hydrochloric acid dropwise with stirring until the oily layer fully dissolves. Pipette 10 mls of hexane into this solution and shake vigorously. Allow the layers to separate and remove the top organic layer. Dry the organic layer with approximately 50-100 mgs of magnesium sulphate. Filter the resulting solution into a HPLC vial and analyse.

The 2-bromobenzyl bromide retention time is 16.7 minutes with a limit of quantitation of 0.00001% (0.1 ppm). The area count for the 2-bromobenzyl bromide peak in the test sample solutions must not exceed the area count for that of the 2-bromobenzyl bromide working standard solution.

In summary, the present invention provides a method of producing pharmaceutical grade bretylium tosylate comprising low amounts of mutagenic impurities. The method comprises forming bretylium tosylate having a purity of less than 99.5% and purifying the bretylium tosylate by: i) forming a slurry of the bretylium tosylate with a mixture of acetone and ethyl acetate; ii) filtering the slurry to obtain purified bretylium tosylate. The bretylium tosylate so produced has a purity of at least 99.5%, and comprises less than 0.5 ppm of the potentially mutagenic impurities ethyl p-toluenesulfonate and 2-bromobenzylbromide, which are used in the formation of the bretylium tosylate and contaminate bretylium tosylate made by certain known methods.

Although a few preferred embodiments have been shown and described, it will be appreciated by those skilled in the art that various changes and modifications might be made without departing from the scope of the invention, as defined in the appended claims.

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention. Typically, when referring to compositions, a composition consisting essentially of a set of components will comprise less than 5% by weight, typically less than 3% by weight, more typically less than 1% by weight of non-specified components.

The term "consisting of" or "consists of" means including the components specified but excluding addition of other components.

Whenever appropriate, depending upon the context, the use of the term "comprises" or "comprising" may also be taken to encompass or include the meaning "consists essentially of" or "consisting essentially of", and may also be taken to include the meaning "consists of" or "consisting of".

For the avoidance of doubt, wherein amounts of components in a composition are described in wt %, this means the weight percentage of the specified component in relation to the whole composition referred to.

The optional features set out herein may be used either individually or in combination with each other where appropriate and particularly in the combinations as set out in the accompanying claims. The optional features for each aspect or exemplary embodiment of the invention as set out herein are also to be read as applicable to any other aspect or exemplary embodiments of the invention, where appropriate. In other words, the skilled person reading this specification should consider the optional features for each exemplary embodiment of the invention as interchangeable and combinable between different exemplary embodiments.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, and drawings), and/or all of the steps of any method or process so disclosed, may be combined in any combination, except combinations where at least some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, and drawings), or to any novel one, or any novel combination, of the steps of any method or process so disclosed.

The invention claimed is:

1. A method of producing bretylium tosylate having a purity of at least 99.5% and comprising less than 0.5 ppm of ethyl p-toluenesulfonate, the method comprising:

a) providing bretylium tosylate having a purity of less than 99.5% by reacting 2-bromo-benzylbromide with dimethylamine to produce (2-bromobenzyl)-dimethylamine and then reacting (2-bromobenzyl)-dimethylamine with ethyl p-toluenesulfonate to produce the bretylium tosylate having a purity of less than 99.5%; and;

b) purifying the bretylium tosylate from step a) by:

i) forming a slurry of the bretylium tosylate from step a) with a mixture of acetone and ethyl acetate;

ii) filtering the slurry to obtain bretylium tosylate; and iii) recrystallizing the bretylium tosylate from step ii) from a mixture of acetone and ethyl acetate to obtain the bretylium tosylate having a purity of at least 99.5%.

2. The method according to claim 1, wherein the mixture of acetone and ethyl acetate in step i) comprises a volume ratio of acetone to ethyl acetate of from 1:1 to 1:5.

3. The method according to claim 1, wherein step i) involves stirring the slurry for at least 20 minutes.

4. The method according to claim 1, wherein steps i) and ii) are repeated at least once.

5. The method according to claim 1, wherein step a) comprises steps:

a1) reacting 2-bromo-benzylbromide with dimethylamine in an organic solvent to form a crude reaction product solution of (2-bromobenzyl)-dimethylamine;

a2) treating the crude reaction product solution of (2-bromobenzyl)-dimethylamine with an aqueous acid to convert the (2-bromobenzyl)-dimethylamine to an acid salt and separating the crude reaction product solution between an organic phase and an aqueous phase;

a3) removing the organic phase from the aqueous phase;

a4) treating the aqueous phase with base to convert the (2-bromobenzyl)-dimethylamine salt to a neutral (2-bromobenzyl)-dimethylamine;

a5) separating the neutral (2-bromobenzyl)-dimethylamine from the aqueous phase to provide purified (2-bromobenzyl)-dimethylamine; and a6) reacting the purified (2-bromobenzyl)-dimethylamine with ethyl p-toluenesulfonate to form the bretylium tosylate having a purity of less than 99.5%.

6. The method according to claim 5, wherein no further purification step is carried out between step a5) and step a6).

7. The method according to claim 5, wherein step a1) involves adding a solution of 2-bromo-benzylbromide to a solution of dimethylamine.

8. The method according to claim 5, wherein the purified bretylium tosylate comprises less than 0.5 ppm 2-bromobenzylbromide.

9. Bretylium tosylate formed by a method of claim 1, the bretylium tosylate having a purity of at least 99.5% and comprising less than 0.5 ppm of ethyl p-toluenesulfonate.

10. Bretylium tosylate according to claim 9 comprising less than 0.5 ppm 2-bromobenzylbromide.

* * * * *